United States Patent [19]
Schleinz

[11] Patent Number: 5,649,918
[45] Date of Patent: Jul. 22, 1997

[54] ABSORBENT ARTICLE HAVING CONTAINMENT GASKETS

[75] Inventor: Alan Francis Schleinz, Appleton, Wis.

[73] Assignee: Kimberly-Clark Corporation, Neenah, Wis.

[21] Appl. No.: 386,588

[22] Filed: Feb. 10, 1995

[51] Int. Cl.$^6$ .................................................. A61F 13/15
[52] U.S. Cl. ............................... 604/385.2; 604/385.1
[58] Field of Search .......................... 604/385.1, 385.2, 604/369

[56] References Cited

U.S. PATENT DOCUMENTS

| | | | |
|---|---|---|---|
| 4,326,528 | 4/1982 | Ryan et al. | 128/287 |
| 4,430,086 | 2/1984 | Repke | 604/385.1 |
| 4,490,148 | 12/1984 | Beckestrom | 604/385 |
| 4,643,728 | 2/1987 | Karami | 604/385 |
| 4,657,539 | 4/1987 | Hasse | 604/385.2 |
| 4,681,579 | 7/1987 | Toussant et al. | 604/385 |
| 4,695,278 | 9/1987 | Lawson | 604/385 |
| 4,704,116 | 11/1987 | Enloe | 604/385 |
| 4,738,677 | 4/1988 | Foreman | 604/385 |
| 4,743,246 | 5/1988 | Lawson | 604/385 |
| 4,753,646 | 6/1988 | Enloe | 604/385.2 |
| 4,795,452 | 1/1989 | Blaney et al. | 604/385.1 |
| 4,808,177 | 2/1989 | DesMarais et al. | 604/385.1 |
| 4,904,251 | 2/1990 | Igaue et al. | 604/385.2 |
| 4,938,755 | 7/1990 | Foreman | 604/385.2 |
| 5,019,067 | 5/1991 | Simmons | 604/385.2 |
| 5,026,364 | 6/1991 | Robertson | 604/385.1 |
| 5,037,415 | 8/1991 | Leroy et al. | 604/385.1 |
| 5,061,261 | 10/1991 | Suzuki et al. | 604/385.2 |
| 5,114,420 | 5/1992 | Igaue et al. | 604/385.2 |
| 5,167,653 | 12/1992 | Igaue et al. | 604/385.2 |
| 5,176,672 | 1/1993 | Bruemmer et al. | 604/385.1 |
| 5,204,997 | 4/1993 | Suzuki et al. | 2/400 |
| 5,209,801 | 5/1993 | Smith | 156/161 |
| 5,224,941 | 7/1993 | Simmons | 604/385.2 |
| 5,236,428 | 8/1993 | Zajaczkowski | 604/385.2 |
| 5,254,111 | 10/1993 | Cancio et al. | 604/385.1 |
| 5,292,316 | 3/1994 | Suzuki | 604/385.2 |
| 5,445,627 | 8/1995 | Mizutani et al. | 604/385.2 |

FOREIGN PATENT DOCUMENTS

| | | |
|---|---|---|
| 0 243 013 A1 | 10/1987 | European Pat. Off. . |
| 0 374 640 A2 | 6/1990 | European Pat. Off. . |
| 0 376 022 A2 | 7/1990 | European Pat. Off. . |
| 0 391 476 A2 | 10/1990 | European Pat. Off. . |
| 0 622 063 A2 | 11/1994 | European Pat. Off. . |
| 2 159 693 | 12/1985 | United Kingdom . |
| 2 250 921 | 6/1992 | United Kingdom . |
| WO93/03698 | 3/1993 | WIPO . |
| WO93/23000 | 11/1993 | WIPO . |

*Primary Examiner*—Robert A. Clarke
*Assistant Examiner*—David J. Cho
*Attorney, Agent, or Firm*—Jeffrey B. Curtin

[57] ABSTRACT

Disclosed is a distinctive absorbent article which includes a pair of stretchable leg containment gaskets. The leg containment gaskets include a bodyfacing surface which extends along a width of the leg containment gaskets and which is adapted to be in a contacting relationship with a wearer's body when in use. An outboard edge of each of the leg containment gaskets is attached to the longitudinal side portions of the absorbent article along an attached width. An inboard edge of each of the leg containment gaskets remains unattached from said longitudinal side portions in at least the crotch portion of the absorbent article along an unattached width. The attached width of each of the leg containment gaskets in the crotch portion of the absorbent article is at least about 30 percent of the width of the leg containment gasket. The absorbent article may also include a pair of stretchable waist containment gaskets. In addition, the absorbent article may include at least one waist flap to provide additional void volume to help contain bodily exudates.

39 Claims, 3 Drawing Sheets

ABSORBENT ARTICLE HAVING CONTAINMENT GASKETS

BACKGROUND OF THE INVENTION

1. Field of the Invention

The present invention relates to an absorbent article which includes containment gaskets. The invention more particularly relates to an absorbent article which uses a composite material to provide containment gaskets which provide a seal against the body of a wearer to prevent leakage of body exudates. The invention also relates to an absorbent article which includes such containment gaskets and at least one waist flap to provide a barrier and additional void volume to contain body exudates.

1. Description of the Related Art

It is desired that absorbent articles such as diapers, training pants or incontinence garments both provide a close, comfortable fit about the wearer and contain body exudates. Absorbent articles typically have elasticized portions at the leg and waist openings to provide an improved fit about the wearer and contain body exudates. For example, conventional absorbent articles generally utilize elastic strands positioned at the leg and waist opening regions to gather the absorbent article and hold it against the body of the wearer. However, absorbent articles having such elasticized portions have commonly failed or leaked at the legs and waist when the wearer has exerted compressive forces on the absorbent article.

Typically, the leakage at the legs and waist is due to a variety of reasons. For example, conventional absorbent articles generally have a relatively small absorbent capacity and a relatively small void volume capacity in the crotch portion. As used herein, the term "void volume" refers to the void volume created between the absorbent article and the wearer when in use. Such void volume is desirable to provide containment of body exudates and, in particular, containment of solid and semi-solid body exudates. The crotch portion of such conventional absorbent articles having a relatively small absorbent capacity and small void volume has become saturated and resulted in excessive pooling of body exudates on the bodyfacing surface of the absorbent article. The pooled exudates can then leak from the leg openings of the absorbent article when compressive forces are exerted by the wearer. Such leakage undesirably soils the outer clothing or bedding of the wearer.

Moreover, insufficient torsional rigidity or stiffness of the leg and waist opening regions of the absorbent articles has resulted in leakage around the leg and waist openings when the wearer has exerted compressive forces on the absorbent article. Elasticized portions which are typically used at the leg and waist opening regions have not had sufficient rigidity and have tended to provide only a relatively small area of contact with the body of the wearer. Such low rigidity and minimal contact has also resulted in an undesirable amount of leakage.

Attempts to alleviate the leakage of fluid have included providing physical barriers such as containment flaps in combination with elastic leg and waist gathers. High-absorbency particles have also been included in the absorbent structure to increase the fluid holding capacity in various regions of the absorbent article.

However, such attempts have not sufficiently reduced the amount of leakage in absorbent articles and, in particular, in absorbent articles which include an absorbent core which has a narrow crotch width. The addition of containment flaps and elastic leg and waist gathers has helped reduce leakage but such absorbent articles have still had an undesirable amount of leakage. Moreover, typical elastic leg and waist gathers have not been sufficiently soft and have tended to irritate the skin of the wearer. Further, many of the containment flaps used have not been sufficiently rigid and have tended to collapse in use. The containment flaps also have not remained sufficiently spaced away from the bodyside surface of the absorbent article to efficiently provide void volume capacity to contain solid body exudates such as feces.

Despite the attempts to develop improved absorbent articles, there remains a need for absorbent articles which better contain bodily exudates when under compressive forces. There is a need for an absorbent article that can effectively provide a soft, conformable seal about the legs and waist of the wearer to better contain body exudates. Moreover, there is a need for an absorbent article which is capable of maintaining sufficient void volume under typical loading conditions.

SUMMARY OF THE INVENTION

In response to the difficulties and problems discussed above, a new absorbent article which has leg containment gaskets and sufficient void volume to contain body exudates has been discovered.

In one aspect, the present invention can provide a distinctive absorbent article which includes a pair of soft leg containment gaskets at the leg opening regions. The absorbent article includes a front portion, a rear portion, a crotch portion which extends between and connects the front portion to the rear portion and a pair of longitudinal side portions. The absorbent article comprises an outer cover, a bodyside liner which is superposed on the outer cover and an absorbent core which is located between the outer cover and the bodyside liner and which has a pair of longitudinal edges.

The absorbent article further comprises a pair of leg containment gaskets which have an inboard edge, an outboard edge, a width, a thickness, a bodyfacing surface which is configured to be in a contacting relationship with a wearer's body when in use, and at least one elongated elastic member which is configured to gather the leg containment gasket when relaxed. The outboard edge of each of the leg containment gaskets is attached to the longitudinal side portions of the absorbent article along an attached width. The inboard edge of each of the leg containment gaskets remains unattached from the longitudinal side portions in at least the crotch portion of the absorbent article along an unattached width. The attached width of each leg containment gasket in the crotch portion of the absorbent article is at least about 30 percent of the total width of each leg containment gasket. In a particular aspect, the absorbent core has a crotch width in the crotch portion of the absorbent article which is less than about 7.08 centimeters.

Each of the leg containment gaskets may comprise a facing layer which provides the bodyfacing surface of the leg containment gasket, a substrate layer which is disposed in a facing relationship with the facing layer and at least one elongated elastic member which is disposed between and attached to at least one of the facing layer and the substrate layer. The elongated elastic member gathers the leg containment gasket when relaxed. In a particular aspect, the inboard edge of each of the leg containment gaskets is located outboard of the longitudinal edges of the absorbent core.

In a further aspect, the absorbent article also comprises a pair of waist containment gaskets which have an inside edge, an outside edge, and a bodyside surface which extends along a width of each of the waist containment gaskets and which is configured to be in a contacting relationship with the wearer's body when in use. The outside edge of each of the waist containment gaskets is attached to the absorbent article and the inside edge of each of the waist containment gaskets remains unattached from the absorbent article along at least a portion of a length of the waist containment gasket.

In another aspect, the present invention can provide an absorbent article which includes a front portion, a rear portion, a crotch portion which extends between and connects the front portion to the rear portion and a pair of longitudinal side portions. The absorbent article comprises an outer cover, a bodyside liner which is superposed on the outer cover, an absorbent core which is located between the outer cover and the bodyside liner and a pair of leg containment gaskets. Each leg containment gasket includes an inboard edge, an outboard edge and a width. The outboard edge of each of the leg containment gaskets is attached to the longitudinal side portions of the absorbent article and the inboard edge of each of the leg containment gaskets remains unattached from the longitudinal side portions of the absorbent article in at least the crotch portion of the absorbent article. The absorbent article further comprises at least one waist flap which includes a proximal edge which is attached to the absorbent article and a distal edge which remains unattached from the bodyside liner of the absorbent article between the inboard edges of the leg containment gaskets.

The distal edge of the waist flap overlaps the inboard edge of each of the leg containment gaskets. The inboard edge of each of the leg containment gaskets is configured to maintain the distal edge of the waist flap in a spaced apart relationship from the bodyside liner and absorbent core of the absorbent article. In a particular aspect, the inboard edge of each of the leg containment gaskets is located outboard of the longitudinal edges of the absorbent core. The waist flap may comprise a nonwoven laminate material which may be liquid impermeable. The waist flap may also include at least one elastic element disposed along the distal edge of the waist flap. In a particular aspect, the elastic element in the waist flap is disposed between the inboard edges of the leg containment gaskets.

The present invention can advantageously provide an absorbent article which includes leg containment gaskets which are capable of efficiently containing bodily exudates while providing a conforming, comfortable fit about the wearer. The leg containment gaskets are configured to provide a sufficient area of sealing contact with the body of a wearer to effectively seal against the leakage of body exudates. The leg containment gaskets and absorbent core of the absorbent article are also configured to provide sufficient void volume to contain body exudates and, in particular, solid and semi-solid body exudates. The present invention can also advantageously provide an absorbent article which includes leg containment gaskets and at least one waist flap which is configured to remain spaced away from the bodyside of the absorbent article to provide additional void volume to contain body exudates. As a result, the absorbent article of the present invention can reduce the amount of leakage around the leg and waist openings of the absorbent article even when the width of the crotch section of the absorbent core of the absorbent article is very narrow.

BRIEF DESCRIPTION OF THE DRAWINGS

The present invention will be more fully understood and further advantages will become apparent when reference is made to the following detailed description of the invention and the accompanying drawings wherein like numerals represent like elements. The drawings are merely representative and are not intended to limit the scope of the appended claims.

DETAILED DESCRIPTION OF THE INVENTION

The present invention provides an absorbent article which includes leg containment gaskets which are configured to efficiently contain body exudates while providing a conforming, comfortable fit about the wearer. The absorbent article may also include an absorbent core which has a relatively narrow crotch width dimension to provide an improved fit about the wearer. Moreover, the absorbent article may include at least one waist flap which is configured to assist in containing body exudates and, in particular, containing solid and semi-solid body exudates.

The absorbent article of the present invention will be described in terms of a diaper article adapted to be worn by infants about the lower torso. It is understood that the absorbent article of the present invention is equally applicable to other articles such as adult incontinent products, training pants, feminine care products and the like.

Figure 1A:
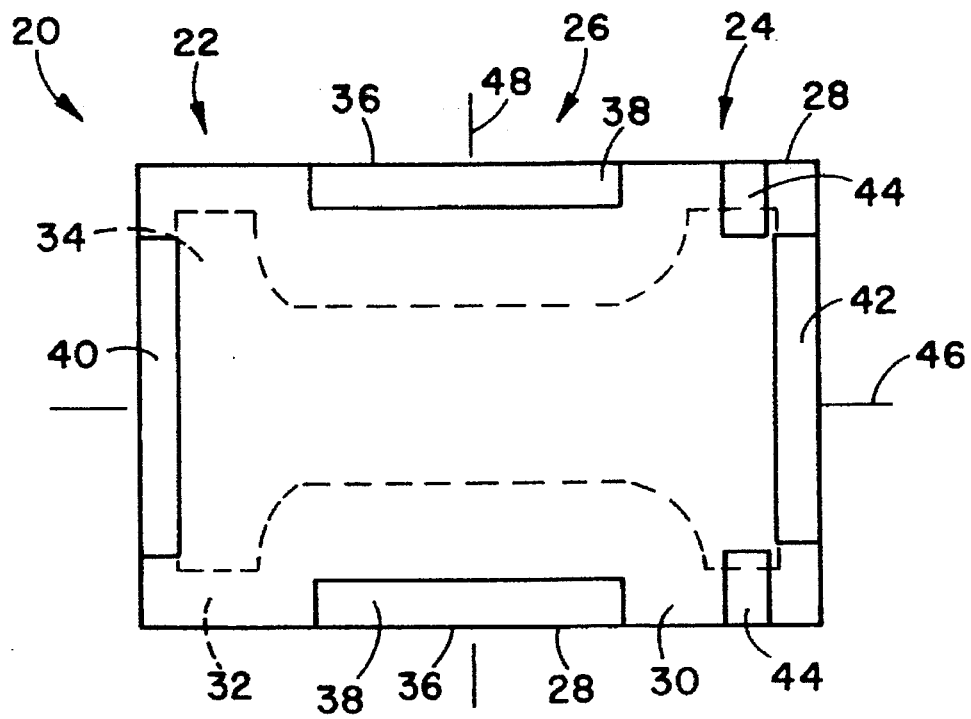
FIG. 1A representatively shows a top plan view of an absorbent article of the present invention.
Figure 1B:
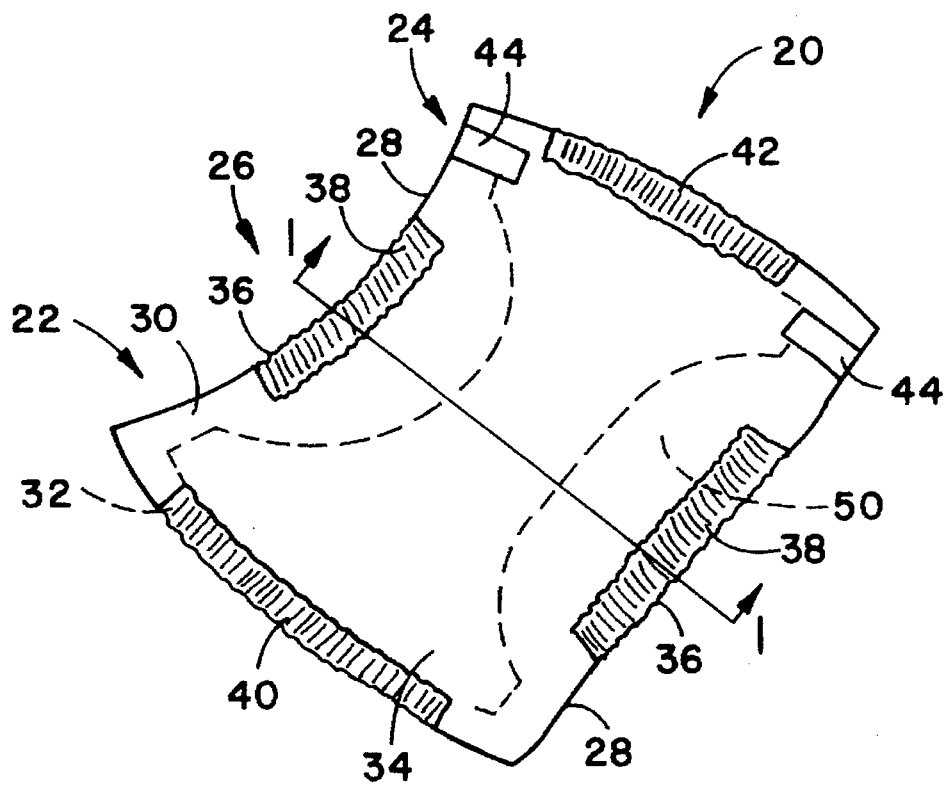
FIG. 1B representatively shows a perspective view of the absorbent article of FIG. 1A wherein the leg and waist containment gaskets have contracted and gathered the side edges of the absorbent article.
Figure 1C:
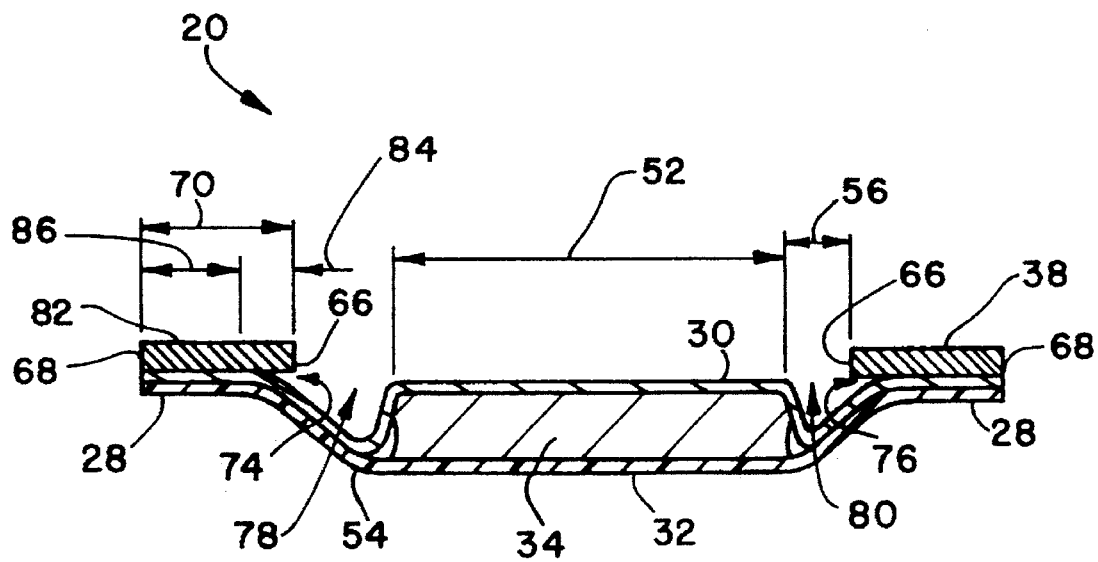
FIG. 1C representatively shows a lateral cross-sectional view of the absorbent article of FIG. 1B taken along line 1—1.

FIGS. 1A–1C representatively illustrate an absorbent article 20 of the present invention. The surface of the article which contacts the wearer is facing the viewer. As representatively illustrated in FIGS. 1A–1C, the absorbent article 20 defines a front portion 22, a rear portion 24, and a crotch portion 26 connecting the front portion 22 and the rear portion 24. The absorbent article 20 includes a bodyside liner 30, an outer cover 32 and an absorbent core 34 located between the bodyside liner 30 and the outer cover 32. The absorbent article 20 also includes a longitudinal centerline 46 and a transverse centerline 48. As used herein, reference to a front portion refers to that part of the absorbent article which is generally located on the front of a wearer when in use, reference to the rear portion refers to the portion of the article generally located at the rear of the wearer when in use, and reference to the crotch portion refers to that portion which is generally located between the legs of the wearer when in use.

The crotch portion 26 has opposite longitudinal side portions 28 which include a pair of longitudinally-extending leg cuffs 36. The leg cuffs 36 are generally adapted to fit about the legs of a wearer in use. The leg cuffs 36 include a pair of leg containment gaskets 38. The absorbent article 20 may further include a front waist containment gasket 40 and a rear waist containment gasket 42. The rear portion 24 of the absorbent article 20 further includes a fastening means 44 which is intended to hold the absorbent article 20 about the waist of the wearer when in use. It should be recognized that individual components of the absorbent article 20 may be optional depending upon the intended use of the absorbent article 20.

Specific examples of disposable diapers on which the different aspects of the present invention may be utilized are also disclosed in the following U.S. patents and U.S. patent applications: U.S. Pat. No. 4,798,603 issued Jan. 17, 1989, to Meyer et al.; U.S. Pat. No. 5,176,668 issued Jan. 5, 1993, to Bernardin; U.S. Pat. No. 5,176,672 issued Jan. 5, 1993, to Bruemmer et al.; U.S. Pat. No. 5,192,606 issued Mar. 9, 1993, to Proxmire et al., and U.S. patent application Ser. No. 08/096,654 filed Jul. 22, 1993, in the name of Hanson et al.

The bodyside liner 30 of the absorbent article 20, as representatively illustrated in FIGS. 1A–1C, suitably presents a bodyfacing surface which is intended to be worn adjacent the body of the wearer and is compliant, soft feeling and nonirritating to the wearer's skin. Further, the bodyside liner 30 may be less hydrophilic than the absorbent core 34, to present a relatively dry surface to the wearer, and may be sufficiently porous to be liquid permeable, permitting liquid to readily penetrate through its thickness. A suitable bodyside liner 30 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner 30 is suitably employed to help isolate the wearer's skin from fluids held in the absorbent core 34.

Various woven and nonwoven fabrics can be used for the bodyside liner 30. For example, the bodyside liner may be composed of a meltblown or spunbonded web of polyolefin fibers. The bodyside liner may also be a bonded-carded web composed of natural and/or synthetic fibers. The bodyside liner may be composed of a substantially hydrophobic material, and the hydrophobic material may, optionally, be treated with a surfactant or otherwise processed to impart a desired level of wettability and hydrophilicity. In a particular embodiment of the present invention, the bodyside liner 30 comprises a nonwoven, spunbond, polypropylene fabric composed of about 2.8–3.2 denier fibers formed into a web having a basis weight of about 22 grams per square meter and a density of about 0.06 grams per cubic centimeter. The fabric is surface treated with about 0.28 weight percent of a surfactant commercially available from Rohm and Haas Co. under the trade designation Triton X-102.

The outer cover 32 of the absorbent article 20, as representatively illustrated in FIGS. 1A–1C, may suitably be composed of a material which is either liquid permeable or liquid impermeable. It is generally preferred that the outer cover 32 be formed from a material which is substantially impermeable to fluids. For example, a typical outer cover can be manufactured from a thin plastic film or other flexible liquid-impermeable material. For example, the outer cover 32 may be formed from a polyethylene film having a thickness of from about 0.012 millimeter (0.5 mil) to about 0.051 millimeter (2.0 mils). If it is desired to present the outer cover 32 with a more clothlike feeling, the outer cover 32 may comprise a polyethylene film having a nonwoven web laminated to the outer surface thereof, such as a spunbond web of polyolefin fibers. For example, a polyethylene film having a thickness of about 0.015 millimeter (0.6 mil) may have thermally laminated thereto a spunbond web of polyolefin fibers, which fibers have a thickness of about 1.5 to 2.5 denier per filament, which nonwoven web has a basis weight of about 24 grams per square meter (0.7 ounce per square yard). Methods of forming such clothlike outer covers are known to those skilled in the art.

Further, the outer cover 32 may be formed of a woven or nonwoven fibrous web layer which has been totally or partially constructed or treated to impart a desired level of liquid impermeability to selected regions that are adjacent or proximate the absorbent core 34. Still further, the outer cover 32 may optionally be composed of a micro-porous "breathable" material which permits vapors to escape from the absorbent core 34 while still preventing liquid exudates from passing through the outer cover 32.

The bodyside liner 30 and outer cover 32 are generally adhered to one another so as to form a pocket in which the absorbent core 34 is located. The bodyside liner 30 and outer cover 32 may be adhered directly to each other around the outer periphery of the absorbent article 20 by any means known to those skilled in the art such as adhesive bonds, sonic bonds or thermal bonds. For example, a uniform continuous layer of adhesive, a patterned layer of adhesive, a sprayed or meltblown pattern of adhesive or an array of lines, swirls or spots of adhesive may be used to affix the bodyside liner 30 to the outer cover 32. Such bonding means may also be suitable for attaching other components of the absorbent article of the present invention together. It should be noted that both the bodyside liner 30 and the outer cover 32 need not extend completely to the outer periphery of the absorbent article. For example, the outer cover 32 may extend to the outer periphery of the absorbent article while the bodyside liner 30 may be attached to the outer cover 32 inboard of the outer periphery, or more towards the longitudinal centerline 46, of the absorbent article.

The leg cuffs 36 are suitably formed by portions of the outer cover 32, and/or bodyside liner 30, which extend beyond the longitudinal sides of the absorbent core 34. The leg cuffs 36 can also be formed from separate materials which are attached to the outer cover 32 and/or bodyside liner 30.

The absorbent core 34, as representatively illustrated in FIGS. 1A–1C, is positioned between the bodyside liner 30 and the outer cover 32 to form the absorbent article 20. The absorbent core 34 is generally conformable and capable of absorbing and retaining body exudates. The absorbent core 34 has a crotch section 50 and longitudinal sides 54.

The absorbent core 34 may have any of a number of shapes and sizes. For example, the composite absorbent core may be rectangular, I-shaped or T-shaped. The size and absorbent capacity of the absorbent core 34 should be compatible with the size of the intended wearer and the fluid loading imparted by the intended use of the absorbent article. It is generally preferred that the absorbent core 34 be narrower in the crotch section 50 of the absorbent core 34 than in the front or back section. It has been found that the absorbent core 34 of the present invention is particularly useful when the crotch width dimension 52 of the crotch section 50 of the absorbent core 34 is from about 2.5 to about 10.2 centimeters (1.0 to about 4.0 inches), desirably no more than about 7.6 centimeters (3.0 inches) and more desirably no more than about 5.1 centimeters (2.0 inches). The narrow crotch width dimension 52 of the crotch section 50 of the absorbent core 34 allows the absorbent article 20 to better fit between the legs of the wearer.

The absorbent core 34 may suitably comprise various types of wettable, hydrophilic fibrous materials. Examples of suitable materials include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester and polyamide fibers; and synthetic fibers composed of a nonwettable thermoplastic polymer, such as polypropylene fibers, which have been hydrophilized by appropriate means known to those skilled in the art. The absorbent core 34 may also comprise selected blends of the various types of fibers mentioned above.

In a particular aspect of the invention, the absorbent core 34 may include a matrix of hydrophilic fibers, such as a web of cellulosic fibers, mixed with particles of a high-absorbency material such as that commonly known as superabsorbent material. As used herein, the term "high-absorbency material" refers to materials that are capable of absorbing at least 10 times their own weight in liquid. In a particular embodiment, the absorbent core 34 comprises a mixture of superabsorbent hydrogel-forming particles and wood pulp fluff. The wood pulp fluff may be exchanged with synthetic, polymeric, meltblown fibers or with a combination of meltblown fibers and natural fibers. The high-absorbency material may be substantially homogeneously mixed with the hydrophilic fibers or may be nonuniformly mixed. The high-absorbency material may also be arranged in a generally discrete layer within the matrix of hydrophilic fibers. Alternatively, the absorbent core 34 may comprise a laminate of fibrous webs and high-absorbency material or other suitable means of maintaining a high-absorbency material in a localized area.

The high-absorbency material can be selected from natural, synthetic and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly(acrylic acid) and poly(methacrylic acid), poly(acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthum gum, locust bean gum, and the like. Mixtures of natural and wholly or partially synthetic absorbent polymers can also be useful in the present invention.

The high-absorbency material may be in any of a wide variety of geometric forms. As a general rule, it is preferred that the high-absorbency material be in the form of discrete particles. However, the high-absorbency material may also be in the form of fibers, flakes, rods, spheres, needles, or the like. Conglomerates of particles of high-absorbency material may also be used. An example of a superabsorbent polymer suitable for use in the present invention is a superabsorbent polymer designated IM5000 which is commercially available from Hoechst-Celanese, a business having offices in Portsmouth, Vir. Other suitable high-absorbency materials may include superabsorbent polymers which are commercially available from Dow Chemical Corp., a business having offices in Midland, Mich.

As a general rule, the high-absorbency material is present in the absorbent core 34 of the present invention in an amount of from about 5 to about 95 weight percent and desirably from about 10 to about 60 weight percent based on the total weight of the absorbent core 34. The distribution of the high-absorbency material within the different portions of the absorbent core 34 can vary depending upon the intended end use of the absorbent core 34.

The fastening means 44 are typically applied to the corners of the rear portion 24 of the absorbent article 20 to provide a means for holding the article 20 on the wearer. Suitable fastening means 44 are well known to those skilled in the art and can include tape tab fasteners, hook and loop fasteners, mushroom and loop fasteners, snaps, pins, belts and the like, and combinations thereof. Typically, the fastening means 44 are configured to be refastenable. It should also be understood that it may be possible to dispense with the fastening means 44 in an absorbent article having a given design configuration.

The leg cuffs 36, as representatively illustrated in FIGS. 1A–1C, include leg containment gaskets 38. Waist containment gaskets 40 and 42 may also be provided. The leg containment gaskets 38 are sufficiently stiff to resist external forces caused by the movements of the wearer while also being conformable to maintain a positive, contacting relationship with the legs of the wearer to effectively reduce or eliminate the leakage of body exudates from the absorbent article 20. In addition, the leg containment gaskets 38 are configured to provide sufficient void volume between the absorbent article 20 and the body of the wearer when in use.

As representatively illustrated in FIGS. 1A–1C and 2, the leg containment gaskets 38 include an inboard edge 66, an outboard edge 68, a width 70 and a thickness 72. As used herein, the term "outboard" refers to a location more remote from the longitudinal centerline 46 of the absorbent article 20 whereas the term "inboard" refers to a location closer to the longitudinal centerline 46 of the absorbent article 20. Each of the leg containment gaskets 38 also includes a bodyfacing surface 82 which is configured to be in a contacting relationship with a wearer's body when in use. The bodyfacing surface 82 of each leg containment gasket 38 generally extends along the width 70 and length of each leg containment gasket 38. Each of the leg containment gaskets 38 also includes at least one elongated elastic member which is configured to gather the leg containment gasket 38 when it is relaxed.

The leg containment gaskets 38 may be of any desired shape and configuration. Suitable shapes include, for example, circular, semicircular, rectangular, triangular, trapezoidal, oblong, dog-boned, hourglass-shaped, or oval. Desirably, the shape of the leg containment gaskets 38 provides a sufficient amount of surface area which is in a contacting relationship with the body of the wearer when in use to provide a seal which better contains body exudates.

For example, at least about 30 percent, desirably at least about 60 percent, more desirably at least about 80 percent and even more desirably at least about 95 percent of the bodyfacing surface 82 of each leg containment gasket 38 is configured to be in a contacting relationship with the wearer's body when in use. In addition, each leg containment gasket 38 is configured to provide at least about 34 square centimeters and desirably at least about 65 square centimeters of contact with the wearer's body when in use for improved performance.

Typically, the width 70 of the leg containment gaskets 38 is at least about 1.0 centimeter, desirably from about 1.5 to about 3.2 centimeters and more desirably from about 1.9 to about 3.0 centimeters to provide an improved gasket or seal about the legs of the wearer. The leg containment gaskets 38 may also extend longitudinally along the entire length of the absorbent article 20 or may only extend partially along the length of the absorbent article 20. When the leg containment gaskets 38 are shorter in length than the absorbent article 20, the leg containment gaskets 38 can be selectively positioned anywhere along the longitudinal side portions of the absorbent article 20. In a particular aspect of the invention, the leg containment gaskets 38 are positioned along the longitudinal side portions 28 primarily in the crotch portion 26 of the absorbent article 20. Each leg containment gasket 38 also has a thickness which is at least about 1 millimeter, desirably at least about 2 millimeters and more desirably from about 3 to about 10 millimeters under a load of 6,900 dynes per square centimeter to provide an improved seal and barrier against the lateral flow of body exudates.

Each leg containment gasket 38 is attached to the longitudinal side portions 28 of the absorbent article 20 such that a channel is formed to contain body exudates. The outboard edge 68 of each of the leg containment gaskets 38 is attached to the longitudinal side portions 28 of the absorbent article 20 while the inboard edge 66 of each of the leg containment gaskets 38 remains unattached from the longitudinal side portions 28 in at least the crotch portion 26 of the absorbent article 20. The leg containment gaskets 38 may be attached to the absorbent article 20 in any of several ways which are well known to those skilled in the art. For example, the gaskets may be ultrasonically bonded, thermally bonded or adhesively bonded to the absorbent article 20. The inboard edge 66 of each of the leg containment gaskets 38 is generally parallel to the longitudinal centerline 46 of the absorbent article 20. The inboard edge 66 of each leg containment gasket 38 is also in a closer proximity to the longitudinal centerline 46 than the outboard edge 68 of each of the leg containment gaskets 38.

As representatively illustrated in FIG. 1C, the outboard edge 68 of each leg containment gasket 38 is attached to the longitudinal side portions 28 of the absorbent article 20 for an attached width 86. In addition, the inboard edge 66 of each leg containment gasket 38 remains unattached from the longitudinal side portions 28 in at least the crotch portion 26 of the absorbent article 20 for an unattached width 84 to provide an undercut. In a particular aspect, the inboard edge 66 of each leg containment gasket 38 remains unattached from the longitudinal side portions 28 along the entire length of the leg containment gasket 38 to provide improved performance. The attached width 86 must be sufficient to ensure that the desired portion of the bodyfacing surface 82 of the leg containment gasket 38 remains in a contacting relationship with the body of the wearer when in use to provide the desired seal to reduce leakage of body exudates. In a particular aspect, the attached width 86 is at least about 30 percent, desirably at least about 60 percent, more desirably at least about 75 percent and even more desirably at least about 90 percent of the total width 70 of the leg containment gasket 38. For example, the attached width 86 of the leg containment gasket 38 may be at least about 1.0 centimeters, desirably at least about 1.4 centimeters, and more desirably from about 1.4 to about 1.6 centimeters. Desirably, the attached width 86 is greater than the unattached width 84 to ensure proper sealing contact with the wearer.

Each leg containment gasket may also be configured such that the inboard edge 66 of the leg containment gasket 38 may be spaced away from the bodyside liner 30 and the outer cover 32 of the absorbent article 20 when in use. As representatively illustrated in FIG. 1C, the inboard edge 66 of each leg containment gasket 38 is desirably spaced away from the bodyside liner 30 and outer cover 32 when in use thereby providing a channel 74 and 76 to better contain body exudates. To provide the channels 74 and 76, the unattached width 84 of each leg containment gasket 38 is at least about 1 millimeter, desirably at least about 2 millimeters and more desirably from about 2 to about 8 millimeters. The unattached width 84 and stiffness of each leg containment gasket 38 ensures that the bodyfacing surface 82 of each leg containment gasket 38 maintains a contacting relationship with the body of the wearer while the bodyside liner 30, outer cover 32 and absorbent core 34 may be spaced away from the body of the wearer.

As representatively illustrated in FIG. 1C, the inboard edge 66 of each of the leg containment gaskets 38 may be located outboard of the longitudinal sides 54 of the absorbent core 34 by a spacing distance 56. By locating the inboard edge 66 of each of the leg containment gaskets 38 outboard of the longitudinal sides 54 of the absorbent core 34, a retention area 78 and 80 is formed on both sides of the absorbent core 34. The retention areas 78 and 80 are configured to act in conjunction with the channels 74 and 76 to provide void volume to contain body exudates thereby improving the performance of the absorbent article. The spacing distance 56 between the inboard edge 66 of each of the leg containment gaskets 38 and the longitudinal sides 54 of the absorbent core 34 should be sufficient to provide void volume to contain body exudates. For example, the spacing distance 56 when the absorbent article 20 is laid out in a flat, untensioned configuration, may be at least about 0.5 centimeters, desirably from about 1.0 to about 4.0 centimeters and more desirably from about 2.0 to about 3.0 centimeters to provide the desired containment.

Each leg containment gasket 38 may also be elongated prior to being attached to the longitudinal side portions 28 of the absorbent article 20. For example, the leg containment gaskets 38 may be elongated at least about 10 percent and desirably from about 20 to about 80 percent before being attached such that the leg containment gaskets 38 gather the longitudinal side portions 28 of the absorbent article 20 when relaxed.

Figure 2:
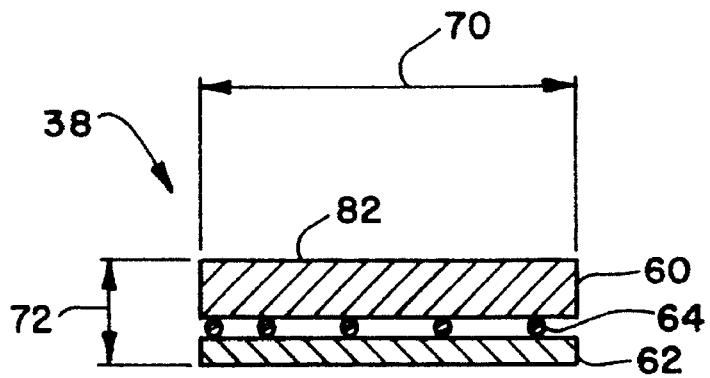
FIG. 2 representatively shows a lateral cross-sectional view of an example of a leg containment gasket of the present invention.

The leg containment gaskets 38 of the present invention, as representatively illustrated in FIGS. 1A–2, have a particularly high stiffness or torsional rigidity to provide the desired seal against the body of the wearer to better contain body exudates. For example, in a particular embodiment, the leg containment gaskets 38 have a Gurley Stiffness of at least about 50 milligrams, desirably at least about 100 milligrams, more desirably from about 100 to about 1100 milligrams and even more desirably from about 300 to about 1100 milligrams. As used herein, the term "Gurley Stiffness" refers to the stiffness value obtained according to the "Gurley Stiffness Test" set forth below in connection with the Examples.

The physical properties of the leg containment gaskets 38 help prevent leakage of bodily exudates when the wearer exerts compressive forces on the absorbent article. In particular, the stiffness of the leg containment gaskets 38 prevents twisting and bunching of the leg openings of the absorbent article which can lead to leaks. In addition, the elasticity and conformability of the leg containment gaskets 38 ensures that the bodyfacing surface 82 of the leg containment gaskets 38 provides an adequate seal against the body of the wearer. The physical properties of the leg containment gaskets of the different aspects of the present invention, such as the thickness and stiffness, also function to space the bodyside liner 30, outer cover 32 and absorbent core 34 away from the wearer's body when in use. As such, void volume is created between the wearer's body and the bodyside liner 30 and absorbent core 34 of the absorbent article 20 to help contain body exudates.

The leg containment gaskets 38 can be made from any material which provides the desired properties. FIG. 2 representatively illustrates a lateral cross-sectional view of one aspect of a leg containment gasket 38 of the present invention. The leg containment gasket 38 includes a facing layer 60 and at least one elastic member 64. The facing layer 60 is configured to provide the bodyfacing surface 82 of the leg containment gasket 38. The elastic members 64 are attached to the facing layer 60 and are configured to gather the leg containment gasket 38 when relaxed. The composite of the facing layer 60 and elastic members 64 may then be attached to the longitudinal side portions 28 of the absorbent article 20, as representatively illustrated in FIGS. 1A–1C. For example, the composite may be attached to the bodyside liner 30 or outer cover 32 of the absorbent article 20.

As representatively illustrated in FIG. 2, each leg containment gasket 38 may also include a substrate layer 62. The substrate layer 62 may be disposed in a facing relationship with the facing layer 60 with the elastic members 64 disposed between the substrate layer 62 and facing layer 60. In such a configuration, the substrate layer 62 is attached to the longitudinal side portions 28 of the absorbent article 20. The facing layer 60 and substrate layer 62 need not have the same dimensions as long as the leg containment gasket 38 has the desired overall width 70.

Many different materials are suitable for use as the facing layer 60. For example, the facing layer 60 can comprise a high loft nonwoven material having a basis weight of from about 15 to about 180 grams per square meter and desirably from about 50 to about 120 grams per square meter. The facing layer 60 may also have a thickness of at least 0.67 millimeters under a pressure 6,900 dynes per square centimeter (0.1 pounds per square inch) and a density of from about 0.02 to about 0.03 grams per cubic centimeter.

In a particular embodiment, the facing layer 60 may be a spunbond fibrous nonwoven web which contains bicomponent fibers which have a diameter of from about 15 to about 30 microns. The bicomponent fibers may be made from polymers such as blends of polyolefins and/or polyolefins and polyesters. For example, the facing layer 60 may include a through-air bonded bicomponent spunbond web which includes polyethylene/polypropylene bicomponent fibers. The facing layer 60 may also include other materials such as cotton, rayon, wood pulp, inherently wettable synthetic polymers, hydrophilized or surface treated polymers and the like. The facing layer 60 may also include other nonwettable materials and materials that are hydrophobic.

When the leg containment gasket 38 includes a substrate layer 62, the substrate layer 62 may include a film or a nonwoven web such as a through-air bonded or point bonded spunbond web or carded web. Generally, the substrate layer 62 has a lower bulk or thickness and a higher density than the facing layer 60. For example, the substrate layer 62 may include a through-air bonded spunbond web which can include bicomponent fibers such as those used in the facing layer 60. The substrate layer 62 may also include a polymeric film such as a 0.5 mil thick polyethylene film which is commercially available under the trade designation LSF-22 from Consolidated Thermoplastics, Inc., a business having offices in Schaumburg, Ill. In a particular aspect of the invention, the substrate layer 62 is provided by the outer cover 32 of the absorbent article 20 and the elastic member 64 and facing layer 60 are attached to the outer cover 32 along the longitudinal side portions 28 of the absorbent article 20.

Materials suitable for use as the elastic member 64 of the leg containment gaskets 38 are known to those skilled in the art. Exemplary of such materials are sheets or strands or ribbons of a polymeric, elastomeric material which are adhered to the facing layer 60 or substrate layer 62 in a stretched position, or which are attached to the facing layer 60 or substrate layer 62 while the layer is pleated, such that elastic constrictive forces are imparted to the layer. The elastic member 64 may also include such materials as polyurethane, synthetic and natural rubber. In a particular aspect of the invention, the elastic members 64 may be composed of individual strands of 940 decitex LYCRA® which are commercially available from E. I. DuPont de Nemours Co., a business having offices in Wilmington, Del. The leg containment gaskets 38 include from about 1 to about 10 elastic members and desirably at least about 6 elastic members per centimeter of width. The elastic members 64 may be elongated prior to being attached to the facing layer 60 or substrate layer 62. For example, the elastic members may be elongated at least about 150 percent and desirably from about 200 to about 500 percent before being attached such that the elastic members 64 gather the leg containment gaskets 38 when relaxed.

The facing layer 60, elastic member 64 and, optionally, the substrate layer 62 may be joined together by any means known to those skilled in the art to provide the leg containment gaskets 38. For example, adhesive, thermal or ultrasonic bonding techniques may be used to join the layers together. A suitable adhesive includes Findley H-2096 hot melt adhesive which is commercially available from Findley Adhesives, Inc., a business having offices located in Wauwatosa, Wis.

In a particular aspect, the leg containment gaskets 38 of the different aspects of the present invention may be provided by the fibrous nonwoven elastic laminate material described in U.S. patent application Ser. No. 08/316,185 filed Sep. 30, 1994, in the name of Yeo et al.

As representatively illustrated in FIGS. 1A–1C, the absorbent article 20 of the present invention may also include waist containment gaskets 40 and 42 to help prevent the leakage of body exudates. Each waist containment gasket 40 and 42 includes an inside edge, an outside edge and a bodyside surface which extends along the width of each of the waist containment gaskets 40 and 42. The bodyside surface of each of the waist containment gaskets 40 and 42 can be configured to be in a contacting relationship with the wearer's body when in use. The outside edge of each waist containment gasket 40 and 42 is attached to the absorbent article 20 while the inside edge of each waist containment gasket 40 and 42 remains unattached from the absorbent article along at least a portion of the length of the waist containment gasket 40 and 42. Similar to the leg containment gaskets 38, a channel may be provided between the unattached inside edge of the waist containment gasket 40 and 42 and the bodyside liner 30 and outer cover 32 of the absorbent article 20 to better contain body exudates. The waist containment gaskets 40 and 42 may be configured similar to and made from the same materials as the leg containment gaskets 38.

The absorbent article of the present invention may also include at least one waist flap to provide more void volume to better contain body exudates. As representatively illustrated in FIGS. 3A–3C, the absorbent article 20 may include a front waist flap 100 and a rear waist flap 102. Each waist flap 100 and 102 has a proximal edge which may be attached to the bodyside liner 30 or outer cover 32 along the outer periphery of the absorbent article 20 and a distal edge 108 and 110 which remains unattached from the absorbent article 20 along at least a portion of the length of the distal edge 108 and 110. The waist flaps 100 and 102 may also have at least one elastic element 104 and 106 disposed along the distal edge of the waist flaps 100 and 102.

Figure 3C:
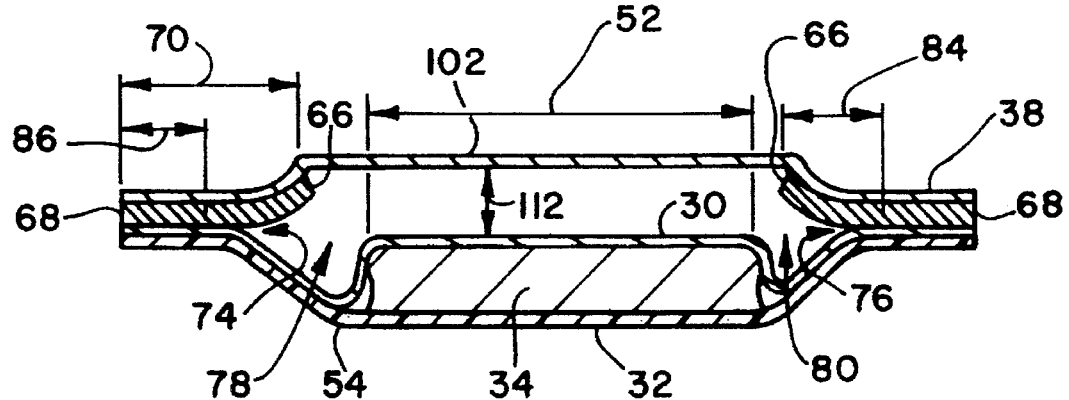
FIG. 3C representatively shows a lateral cross-sectional view of the absorbent article of FIG. 3B taken along line 3—3.
Figure 3A:
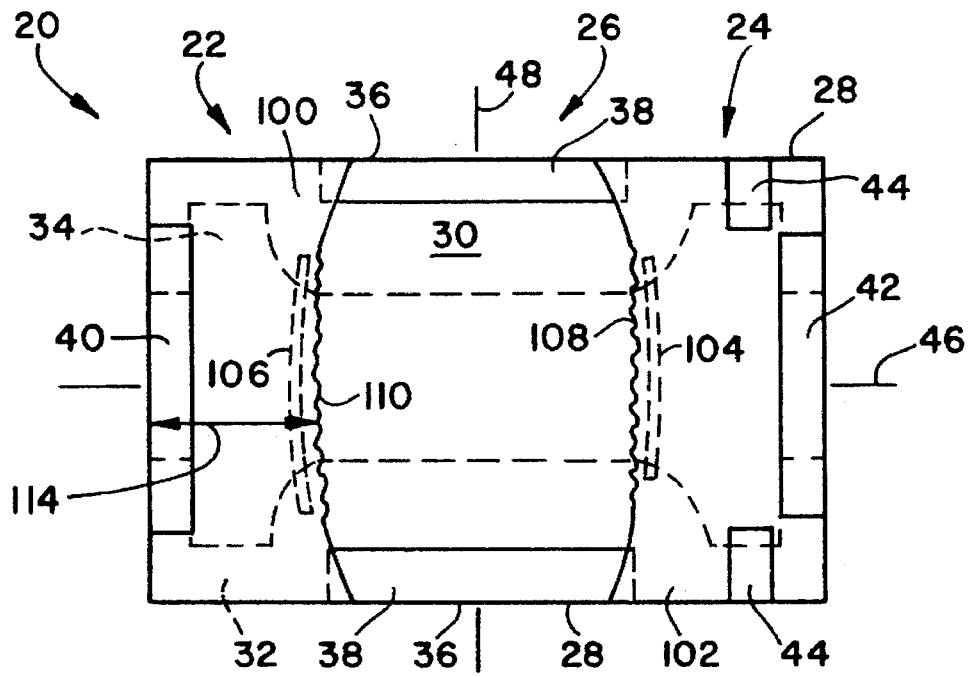
FIG. 3A representatively shows a top plan view of another absorbent article of the present invention.
Figure 3B:
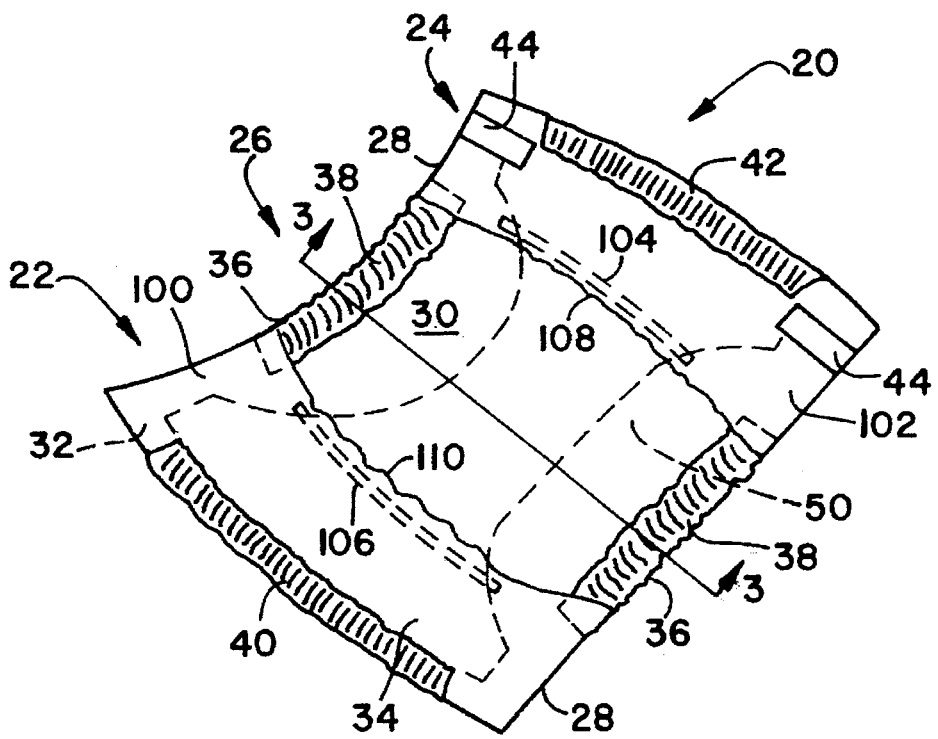
FIG. 3B representatively shows a perspective view of the absorbent article of FIG. 3A wherein the leg and waist containment gaskets have contracted and gathered the side edges of the absorbent article.

As representatively illustrated in FIGS. 3A–3C, the distal edges 108 and 110 of the waist flaps 100 and 102 may be configured to overlap the inboard edges 66 of each of the leg containment gaskets 38. For example, the waist flap may be adhesively attached to the bodyfacing surface 82 of each leg containment gasket 38 such that the waist flap overlaps each leg containment gasket 38. In such a configuration, the distal edges 108 and 110 of each waist flap 100 and 102 remain unattached from the absorbent article 20 between the inboard edges 66 of the leg containment gaskets 38. By attaching the waist flap to the leg containment gaskets in such a manner, the waist flaps are maintained in a spaced apart relationship from the bodyside liner 30 and absorbent core 34. The combination of the leg containment gaskets 38 and waist flaps 100 and 102 effectively provides a seal about the entire outer periphery of the absorbent article 20 to reduce leakage of body exudates.

When the leg containment gaskets 38 are used to space the waist flap away from the bodyside liner 30 and absorbent core 34, it is desirable that the unattached width 84 of the leg containment gaskets 38 be such that the inboard edges 66 of the leg containment gaskets 38 tend to curve upwards as representatively illustrated in FIG. 3C. For example, in this configuration, the unattached width 84 may be at least about 5 millimeters and desirably from about 5 to about 8 millimeters. In addition, the stiffness and rigidity of each leg containment gasket 38 assists in maintaining the waist flaps 100 and 102 in the spaced apart relationship from the bodyside liner 30 and absorbent core 34 when in use.

In use, such waist flaps 100 and 102 are configured to be positioned in a contacting relationship with the wearer's body. For example, as representatively illustrated in FIG. 3C, a spaced apart distance 112 between the waist flap 102 and the bodyside liner 30 and absorbent core 34 may provide an area of void volume to help contain body exudates and prevent body exudates from leaking through the waist areas of the absorbent article 20. The spaced apart distance 112 may be any distance which provides the desired void volume for containment. For example, the spaced apart distance 112 may be at least about 0.1 centimeters and desirably from about 0.2 to about 1.0 centimeters.

Any materials which provide the desired performance are suitable for use as the waist flaps 100 and 102 of the present invention. For example, the waist flaps 100 and 102 can comprise a nonwoven material, such as a stretch bonded laminate having a basis weight of from about 100 to about 200 grams per square meter. Desirably, the waist flaps 100 and 102 are also liquid impermeable.

Materials suitable for use as the elastic elements 104 and 106 of the waist flaps 100 and 102 are known to those skilled in the art. Exemplary of such materials are strands or ribbons of a polymeric, elastomeric material which are adhered to the waist flaps 100 and 102 in a stretched position, or which are attached to the waist flaps while the waist flaps are pleated, such that elastic constrictive forces are imparted to the waist flaps. In a particular aspect of the invention, the elastic elements 104 and 106 may be composed of individual strands of 940 decitex LYCRA® which are available from E. I. DuPont de Nemours Co., a business having offices in Wilmington, Del. Typically, the elastic elements 104 and 106 are elongated prior to being attached to the waist flaps. For example, the elastic elements may be elongated at least about 5 percent and desirably from about 10 to about 80 percent before being attached such that the elastic elements 104 and 106 gather the waist flaps 100 and 102 when relaxed.

The elastic elements 104 and 106 may or may not extend completely across a width of the waist flaps 100 and 102. In a particular aspect as representatively illustrated in FIGS. 3A–3C, the elastic elements 104 and 106 only extend between the inboard edges 66 of the leg containment gaskets 38. By only being attached between the leg containment gaskets 38, the elastic forces imparted on the longitudinal side portions 28 of the absorbent article 20 by the elastic elements 104 and 106 are minimized.

The waist flaps 100 and 102 may be of any desired shape and configuration. Typically, the proximal edges of the waist flaps are configured to be attached to the outer periphery of the absorbent article 20. Each waist flap 100 and 102 has a length 114 along the longitudinal centerline 46 of the absorbent article 20 which allows the waist flap to contain body exudates. Desirably, the length 114 of each waist flap is at least about 1.0 centimeters, desirably from about 1.5 to about 8.0 centimeters and more desirably from about 2.0 to about 5.0 centimeters to provide sufficient void volume to contain body exudates and, in particular, solid and semi-solid body exudates.

The different aspects of the present invention can advantageously provide an absorbent article having a pair of leg containment gaskets which are capable of efficiently maintaining sealing contact with a wearer's body to more effectively prevent leakage of body exudates. Moreover, the absorbent article can also include waist flaps which can be configured to provide additional void volume to help contain body exudates and prevent body exudates from leaking. In particular, the combination of the leg containment gaskets and the waist flaps can provide a seal about the entire outer periphery of the absorbent article. As a result, the absorbent article of the present invention can reduce the amount of leakage around the leg and waist openings of the absorbent article even when the width of the crotch section of the absorbent core of the absorbent article is very narrow.

EXAMPLES

The following examples are presented to provide a more detailed understanding of the invention. The particular materials and parameters are exemplary and are not intended to limit the scope of the invention.

Gurley Stiffness Test

This test is designed to measure the force, in milligrams, required to bend a sample of material under specific conditions. The recorded force constitutes a measurement of the stiffness of the material.

Equipment & Materials
1. Gurley Digital Stiffness Tester which is commercially available from Teledyne Gurley, a business having offices in Troy, N.Y.
2. Weights of 5, 25, 50 and 200 grams commercially available from Teledyne Gurley.
3. Paper Cutter Test Procedure
1. Calibrate the Gurley Digital Stiffness Tester.
2. Cut the sample material using the paper cutter to provide a 1.0 inch ×1.5 inch sample.
3. Position the sample in the Gurley Digital Stiffness Tester such that the sample is centered over the pendulum. The sample will overlap the top of the pendulum by 0.25 inches and 0.25 inches will be held in the jaws of the tester.
4. Set the amount of weight and its position depending upon the relative stiffness of the sample.
5. Start the tester in motion.
6. Record the average scale reading.

Example 1

Five samples of a material which can be used to provide the leg containment gaskets of the present invention were made. As representatively illustrated in FIG. 2, the material included a facing layer 60 which was a through-air bonded bicomponent spunbond web of polyethylene/polypropylene bicomponent fibers having a basis weight of about 33.9 grams per square meter. The elastic member 64 comprised a urethane film having a thickness of 1.0 mils which was commercially available from Deerfield Urethane, a business having offices located in South Deerfield, Mass., under the trade designation PT-6100 which was elongated 300 percent prior to attachment. The leg containment gasket material did not include a substrate layer. The leg containment gasket material had a thickness of 1.47 millimeters under a pressure of 6,900 dynes per square centimeter (0.1 pounds per square inch). The samples were then subjected to the Gurley Stiffness Test described above. The samples had an average Gurley Stiffness of 53.17 milligrams.

Example 2

Five samples of a material which can be used to provide the leg containment gaskets of the present invention were made. As representatively illustrated in FIG. 2, the material included a facing layer 60 which was a through-air bonded bicomponent spunbond web of polyethylene/polypropylene bicomponent fibers having a basis weight of about 102 grams per square meter. The substrate layer 62 was a through-air bonded bicomponent spunbond web of polyethylene/polypropylene bicomponent fibers having a basis weight of about 16.9 grams per square meter. The elastic member 64 included individual strands of 940 decitex LYCRA® which were commercially available from E. I. DuPont de Nemours Co., a business having offices in Wilmington, Del. The material had about 3.1 elastic strands per centimeter of width which had been elongated 300 percent prior to attachment. The leg containment gasket material had a thickness of 3.81 millimeters under a pressure of 6,900 dynes per square centimeter (0.1 pounds per square inch). The samples were then subjected to the Gurley Stiffness Test described above. The samples had an average Gurley Stiffness of 1034.5 milligrams.

Comparative Example 1

Five samples of the elastic material used for the elasticized leg cuffs on Step 2 sized HUGGIES® SUPREME diapers, which were commercially available from Kimberly-Clark Corporation, a business having offices located in Neenah, WI, were obtained. The elastic material included a layer of 0.75 mil polypropylene film material which was commercially available from Edison Plastics Company, a business having offices located in South Plainfield, N.J. The elastic material also included four strands of 940 decitex LYCRA® which was commercially available from E. I. DuPont de Nemours Co., a business having offices in Wilmington, Del. The elastic strands were stretched 200–350 percent before being adhesively secured to the film layer. The elastic material was subjected to the Gurley Stiffness Test as described above. The elastic material had an average Gurley Stiffness of 21.2 milligrams.

Comparative Example 2

Five samples of Step 5 sized HUGGIES® SUPREME diapers, which were commercially available from Kimberly-Clark Corporation were obtained. The diapers included elasticized containment flaps which extend longitudinally along the bodyside liner of the diaper and which are configured to remain in a generally perpendicular and upright configuration from the bodyside liner. The elasticized containment flaps included a nonwoven laminate which is a meltblown film having a spunbond web laminated thereto on both sides. The flaps also included two strands of 470 decitex LYCRA® which was commercially available from E. I. DuPont de Nemours Co., a business having offices in Wilmington, Del. The elasticized containment flaps were removed from the diapers, allowed to relax and subjected to the Gurley Stiffness Test as described above. The samples had an average Gurley Stiffness of 13.3 milligrams.

While the invention has been described in detail with respect to specific aspects thereof, it will be appreciated that those skilled in the art, upon attaining an understanding of the foregoing, may readily conceive of alterations to, variations of, and equivalents to these aspects. Accordingly, the scope of the present invention should be assessed as that of the appended claims and any equivalents thereto.

I claim:

1. An absorbent article which includes a front portion, a rear portion, a crotch portion which extends between and connects said front portion to said rear portion and a pair of longitudinal side portions, said absorbent article comprising:
   a) an outer cover;
   b) a bodyside liner which is superposed on said outer cover;
   c) an absorbent core which is located between said outer cover and said bodyside liner and which includes a pair of longitudinal edges; and
   d) a pair of leg containment gaskets, each of which includes an inboard edge, an outboard edge, a width, a thickness, a bodyfacing surface which is configured to be in a contacting relationship with a wearers body when in use and at least one elongated elastic member which is configured to gather said leg containment gasket when relaxed, wherein said outboard edge is attached to said longitudinal side portions of said absorbent article along a substantially continuous attached width and said inboard edge remains unattached from said longitudinal side portions in at least said crotch portion of said absorbent article along an unattached width and wherein said substantially continuous attached width of each of said leg containment gaskets in said crotch portion of said absorbent article is at least about 60 percent of said width of each of said leg containment gaskets.

2. The absorbent article according to claim 1 wherein said absorbent core includes a crotch width in said crotch portion of said absorbent article which is no more than about 7.6 centimeters.

3. The absorbent article according to claim 1 wherein said thickness of each of said leg containment gaskets is at least about 1.0 millimeters.

4. The absorbent article according to claim 1 wherein said attached width of each of said leg containment gaskets in said crotch portion of said absorbent article is at least about 75 percent of said width of each of said leg containment gaskets.

5. The absorbent article according to claim 1 wherein said width of each of said leg containment gaskets is at least about 1.0 centimeters.

6. The absorbent article according to claim 1 wherein said attached width of each of said leg containment gaskets in said crotch portion of said absorbent article is at least about 1.0 centimeters.

7. The absorbent article according to claim 1 wherein said unattached width of each of said leg containment gaskets in said crotch portion of said absorbent article is at least about 1 millimeter.

8. The absorbent article according to claim 1 wherein said attached width of each of said leg containment gaskets in said crotch portion of said absorbent article is greater than said unattached width of each of said leg containment gaskets in said crotch portion of said absorbent article.

9. The absorbent article according to claim 1 wherein said inboard edge of each of said leg containment gaskets is located outboard of said longitudinal edges of said absorbent core.

10. The absorbent article according to claim 9 wherein a spacing distance between said inboard edge of each of said leg containment gaskets and said longitudinal edges of said absorbent core is at least about 0.5 centimeters.

11. The absorbent article according to claim 1 wherein at least about 30 percent of said bodyfacing surface of each of said leg containment gaskets is configured to be in a contacting relationship with said wearer's body when in use.

12. The absorbent article according to claim 1 wherein each of said leg containment gaskets is configured to provide at least about 34 square centimeters of contact with said wearer's body when in use.

13. The absorbent article according to claim 1 wherein said inboard edge of each of said leg containment gaskets is configured to provide a channel to contain body exudates.

14. The absorbent article according to claim 1 wherein said at least one elastic member of each of said leg containment gaskets is elongated at least about 150 percent before being attached to said leg containment gasket.

15. The absorbent article according to claim 1 wherein each of said leg containment gaskets is elongated from at least about 10 percent before being attached to said longitudinal side portions of said absorbent article.

16. The absorbent article according to claim 1 wherein said at least one elastic member of each of said leg containment gaskets comprises at least one strand of elastic.

17. The absorbent article according to claim 1 wherein each of said leg containment gaskets comprises:
   i) a facing layer which provides said bodyfacing surface of said leg containment gasket;
   ii) a substrate layer which is disposed in a facing relationship with said facing layer; and
   iii) said at least one elongated elastic member which is disposed between and attached to at least one of said facing layer and said substrate layer.

18. The absorbent article according to claim 17 wherein said facing layer of each of said leg containment gaskets comprises a through-air bonded bicomponent spunbond web.

19. The absorbent article according to claim 17 wherein said substrate layer of each of said leg containment gaskets is provided by said outer cover of said absorbent article.

20. The absorbent article according to claim 1 wherein each of said leg containment gaskets has a Gurley Stiffness of at least about 50 milligrams.

21. The absorbent article according to claim 1 wherein each of said leg containment gaskets has a Gurley Stiffness of at least about 100 milligrams.

22. The absorbent article according to claim 1 wherein said longitudinal side portions of said absorbent article are in a parallel relationship thereby providing said absorbent article with a substantially rectangular configuration.

23. The absorbent article according to claim 1 wherein each of said leg containment gaskets is configured to space said absorbent core away from said wearer's body when in use.

24. An absorbent article which includes a front portion, a rear portion, a crotch portion which extends between and connects said front portion to said rear portion and a pair of longitudinal side portions, said absorbent article comprising:
   a) an outer cover;
   b) a bodyside liner which is superposed on said outer cover;
   c) an absorbent core which is located between said outer cover and said bodyside liner and which includes a pair of longitudinal edges;
   d) a pair of leg containment gaskets, each of which includes an inboard edge, an outboard edge, a width, a thickness, a bodyfacing surface which is configured to be in a contacting relationship with a wearers body when in use and at least one elongated elastic member which is configured to gather said leg containment gasket when relaxed, wherein said outboard edge is attached to said longitudinal side portions of said absorbent article along a substantially continuous attached width and said inboard edge remains unattached from said longitudinal side portions in at least said crotch portion of said absorbent article along an unattached width and wherein said substantially continuous attached width of each of said leg containment gaskets in said crotch portion of said absorbent article is at least about 60 percent of said width of each of said leg containment gaskets; and
   e) at least one waist containment gasket which includes an inside edge, an outside edge, and a bodyside surface which extends along a width of said waist containment gasket and which is configured to be in a contacting relationship with said wearer's body when in use wherein said outside edge is attached to said absorbent article and said inside edge remains unattached from said absorbent article along at least a portion of a length of said waist containment gasket.

25. An absorbent article which includes a front portion, a rear portion, a crotch portion which extends between and connects said front portion to said rear portion and a pair of longitudinal side portions, said absorbent article comprising:
   a) an outer cover;
   b) a bodyside liner which is superposed on said outer cover;
   c) an absorbent core which is located between said outer cover and said bodyside liner and which includes a pair of longitudinal edges;
   d) a pair of leg containment gaskets, each of which include an inboard edge, an outboard edge and a width wherein said outboard edge is attached to said longitudinal side portions of said absorbent article along a substantially continuous attached width and said inboard edge remains unattached from said longitudinal side portions in at least said crotch portion of said absorbent article along an unattached width and wherein said substantially continuous attached width of each of said leg containment gaskets in said crotch portion of said absorbent article is at least about 60 percent of said width of each of said leg containment gaskets; and e) at least one waist flap which includes a proximal edge which is attached to said absorbent article and a distal edge which is configured to overlap said inboard edge of each of said leg containment gaskets and which remains unattached from said bodyside liner of said absorbent article between said inboard edges of said leg containment gaskets wherein said inboard edge of each of said leg containment gaskets is configured to maintain said distal edge of said waist flap in a spaced apart relationship from said bodyside liner.

26. The absorbent article according to claim 25 wherein said absorbent core includes a crotch width in said crotch portion of said absorbent article which is less than about 7.6 centimeters.

27. The absorbent article according to claim 25 wherein said attached width of each of said leg containment gaskets in said crotch portion of said absorbent article is at least about 75 percent of said width of each of said leg containment gaskets.

28. The absorbent article according to claim 25 wherein said attached width of each of said leg containment gaskets in said crotch portion of said absorbent article is at least about 1.0 centimeters.

29. The absorbent article according to claim 25 wherein said unattached width of each of said leg containment gaskets in said crotch portion of said absorbent article is at least about 1 millimeter.

30. The absorbent article according to claim 25 wherein said attached width of each of said leg containment gaskets in said crotch portion of said absorbent article is greater than said unattached width of each of said leg containment gaskets in said crotch portion of said absorbent article.

31. The absorbent article according to claim 25 wherein said inboard edge of each of said leg containment gaskets is located outboard of said longitudinal edges of said absorbent core.

32. The absorbent article according to claim 25 wherein said inboard edge of each of said leg containment gaskets is configured to provide a channel to contain body exudates.

33. The absorbent article according to claim 25 wherein each of said leg containment gaskets comprises:

i) a facing layer which provides said bodyfacing surface of said leg containment gasket;

ii) a substrate layer which is disposed in a facing relationship with said facing layer; and iii) at least one elongated elastic member which is disposed between and attached to at least one of said facing layer and said substrate layer wherein said at least one elastic member is configured to gather said leg containment gasket when relaxed.

34. The absorbent article according to claim 25 wherein each of said leg containment gaskets has a Gurley Stiffness of at least about 50 milligrams.

35. The absorbent article according to claim 25 wherein said at least one waist flap is liquid impermeable.

36. The absorbent article according to claim 25 wherein said at least one waist flap comprises a nonwoven laminate material.

37. The absorbent article according to claim 25 wherein said at least one waist flap includes at least one elastic element disposed along said distal edge of said at least one waist flap.

38. The absorbent article according to claim 37 wherein said at least one elastic element is disposed between said inboard edge of each of said leg containment gaskets.

39. The absorbent article according to claim 37 wherein said at least one elastic element comprises a strand of elastic.

\* \* \* \* \*